(12) United States Patent
Al-Terki

(10) Patent No.: US 9,919,133 B1
(45) Date of Patent: Mar. 20, 2018

(54) SURGICAL DRAIN ANCHORING DEVICE

(71) Applicant: Abdullatif E. A. H. Al-Terki, Safat (KW)

(72) Inventor: Abdullatif E. A. H. Al-Terki, Safat (KW)

(*) Notice: Subject to any disclaimer, the term of this patent is extended or adjusted under 35 U.S.C. 154(b) by 0 days.

(21) Appl. No.: 15/814,299

(22) Filed: Nov. 15, 2017

Related U.S. Application Data

(60) Provisional application No. 62/439,857, filed on Dec. 28, 2016.

(51) Int. Cl.
  *A61M 5/32* (2006.01)
  *A61M 25/02* (2006.01)
  *A61F 5/445* (2006.01)
  *A61M 1/00* (2006.01)

(52) U.S. Cl.
  CPC .............. *A61M 25/02* (2013.01); *A61F 5/445* (2013.01); *A61M 1/0088* (2013.01); *A61M 2025/024* (2013.01); *A61M 2025/0246* (2013.01); *A61M 2025/0266* (2013.01)

(58) Field of Classification Search
  CPC .......... A61M 25/02; A61M 2025/0206; A61M 2025/0213; A61M 2025/0253; A61M 2025/028; A61M 2025/0293; A61M 2025/024; A61M 2025/0246; A61M 2025/0266; A61M 1/0008; A61M 1/0088; A61M 1/0086; A61F 5/445; A61F 5/448
  USPC ........................................................ 604/174
  See application file for complete search history.

(56) References Cited

U.S. PATENT DOCUMENTS

| | | | |
|---|---|---|---|
| 2,898,917 A | 8/1959 | Wallace | |
| 3,076,458 A | 2/1963 | Mason | |
| 4,533,349 A | 8/1985 | Bark | |
| 4,579,120 A | 4/1986 | MacGregor | |
| 4,586,927 A * | 5/1986 | Jensen | A61F 5/442 604/334 |
| 4,645,492 A * | 2/1987 | Weeks | A61M 25/02 128/DIG. 26 |
| 4,717,385 A | 1/1988 | Cameron et al. | |
| 4,874,380 A | 10/1989 | Hesketh | |
| 4,929,245 A | 5/1990 | Holtermann et al. | |
| 4,959,055 A | 9/1990 | Hillyer | |

(Continued)

FOREIGN PATENT DOCUMENTS

CN  101015715 A  8/2007

*Primary Examiner* — Jason Flick
(74) *Attorney, Agent, or Firm* — Richard C. Litman

(57) ABSTRACT

The surgical drain anchoring device includes a resilient, flexible pad having an upper surface, an opposing lower surface, a centrally positioned aperture, and a slit extending radially outward from the aperture to the perimeter of the device. A neck member positioned on the upper surface defines a central channel aligned with the aperture, and a tapered member aligned with the aperture extends from the lower surface so that a surgical drain can pass through the neck, the aperture, and the tapered member. An outer ridge member adapted for attachment of an external drainage bag thereto also extends from the upper surface. The external drainage bag includes a primary opening configured to attach onto the outer ridge member and a secondary opening configured to drain fluid from the drainage bag. The device can also include a strap, tie, or clip configured for securing the neck around the surgical drain.

12 Claims, 8 Drawing Sheets

(56) References Cited

U.S. PATENT DOCUMENTS 5,833,666 A * 11/1998 Davis .................... A61M 25/02
                                                128/DIG. 26
2007/0282271 A1    12/2007  Kaplan et al.

* cited by examiner

SURGICAL DRAIN ANCHORING DEVICE

CROSS-REFERENCE TO RELATED APPLICATION

This application claims the benefit of U.S. Provisional Patent Application Ser. No. 62/439,857, filed Dec. 28, 2016, which is herein incorporated by reference in its entirety.

BACKGROUND

1. Field

The disclosure of the present patent application relates to a medical fluid drainage apparatus, and particularly to a surgical drain anchoring device for supporting a surgical drain against the skin of a patient.

2. Description of the Related Art

Typically surgical drains are used to prevent and relieve the accumulation of gas and/or fluid, as well as to allow air or other gases to exit from a body cavity and liquids (such as pus, blood, serous exudates, as well as chyle or bile) to drain freely. Surgical drains can also be used to form a controlled fistula, such as after common bile duct exploration, and to provide a tract that acts as a drain (such as a nephrostomy tube for the kidney), if obstructed distally.

While there are a number of benefits associated with the use of surgical drains, adverse issues may arise from the use of such surgical drains. For example, unintentionally blocking the surgical drain, such as kinking the surgical drain, incorrectly positioning the surgical drain, selecting the wrong size surgical drain, or dislodging (i.e., accidentally removing) the surgical drain, may lead to an increased risk of infection, as well as the potential accumulation of fluids in a body cavity that can adversely affect, if not delay, the healing process. Further, failure to properly drain a wound can risk impairing the function of an organ, especially if using a surgical drain is the only way in which the excess gas and/or liquid can drain.

Thus, a surgical drain anchoring device solving the aforementioned problems is desired.

SUMMARY

The surgical drain anchoring device includes a resilient, flexible pad having an upper surface, an opposing lower surface, a centrally positioned aperture, and a slit extending radially outward from the aperture to the perimeter of the device. A neck member positioned on the upper surface defines a central channel aligned with the aperture, and a tapered member aligned with the aperture extends from the lower surface so that a surgical drain can pass through the neck, the aperture, and the tapered member. An outer ridge member adapted for attachment of an external drainage bag thereto also extends from the upper surface. The external drainage bag includes a primary opening configured to attach onto the outer ridge member and a secondary opening configured to drain fluid from the drainage bag. The device also includes a strap, tie, or clip configured for securing the neck around the surgical drain.

These and other features of the present invention will become readily apparent upon further review of the following specification and drawings.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 4:
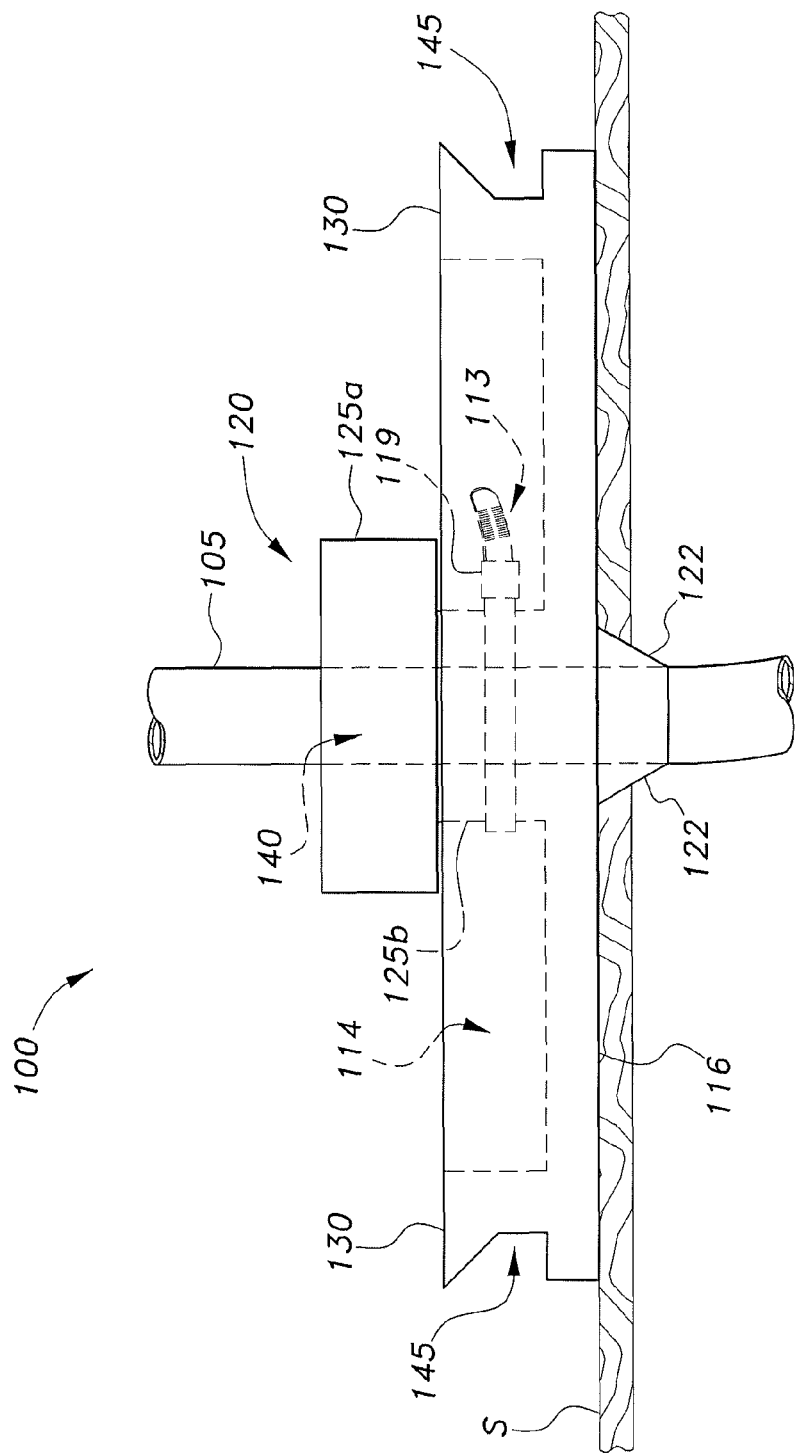
FIG. 4 is an environmental elevation view of the surgical drain anchoring device of FIG. 2, shown with the patient's skin in section.

Referring to FIGS. 1-7B, a surgical drain anchoring device 100 for safely and securely supporting a surgical drain 105 against the skin S of a patient P is generally illustrated. The device 100 includes a resilient, flexible pad having an upper surface 114 and an opposing lower surface 116, the opposing lower surface 116 being configured for attaching onto the skin S of the patient P (e.g., by a layer of biocompatible adhesive or by suturing), as well as a centrally positioned aperture 111 (FIG. 6) and a slit 112 extending radially outward from the aperture 111 to the perimeter of the device 100, so that the device 100 can be opened to receive the surgical drain 105, as illustrated by the gap A in FIG. 2, and then approximated to secure the device 100 around the surgical drain 105 (e.g., catheter tubing), as illustrated by the seam A' in FIG. 3. The device 100 further includes a neck member 120 extending from the center of the upper surface 114 of the pad, the neck member 120 having a central channel 140 aligned with the aperture 111 of the device 100 through which the surgical drain 105 exiting from the skin S of the patient P can pass, and an annular tapered member 122 aligned with the aperture 111 that extends from the lower surface 116 so that a surgical drain can pass through the neck 120, the aperture 111, and the tapered member 122, as illustrated in FIG. 4. The device 100 also includes an outer ridge member 130 adapted for receiving an external drainage bag 150. The external drainage bag 150 may include a primary opening 200 configured for attaching onto the outer ridge member 130, and a secondary opening 215, such as a valve, configured for draining the fluid from the external drainage bag 150 once the fluid reaches a predetermined level. The device 100 also includes a strap 113 similar to a cable tie for securing the device 100 around the surgical drain 105.

The surgical drain 105, such as a catheter tube, can be any type of surgical drain known in the art and can be formed from any suitable, flexible medical grade material, such as nylon. The surgical drain 105 allows air or other gases to exit a body cavity and/or liquids (such as blood, serum, pus, urine, feces, bile and/or lymph) that may collect at the site of the operation or in a wound to drain. The surgical drain 105 can be either an open surgical drain, wherein the fluid drain can drain freely, such as onto a gauze pad, or a closed surgical drain, wherein the fluid can drain freely into a container, such as the external drainage bag 150 or a bottle. Further, the surgical drain 105 may be an active surgical drain, wherein the drainage is achieved under suction, or a passive surgical drain, wherein the gas and/or liquid is drained through the surgical drain 105 due to the pressure gradient between the body cavity and the exterior of the body cavity, due to overflow, and/or due to gravity.

Figure 5:
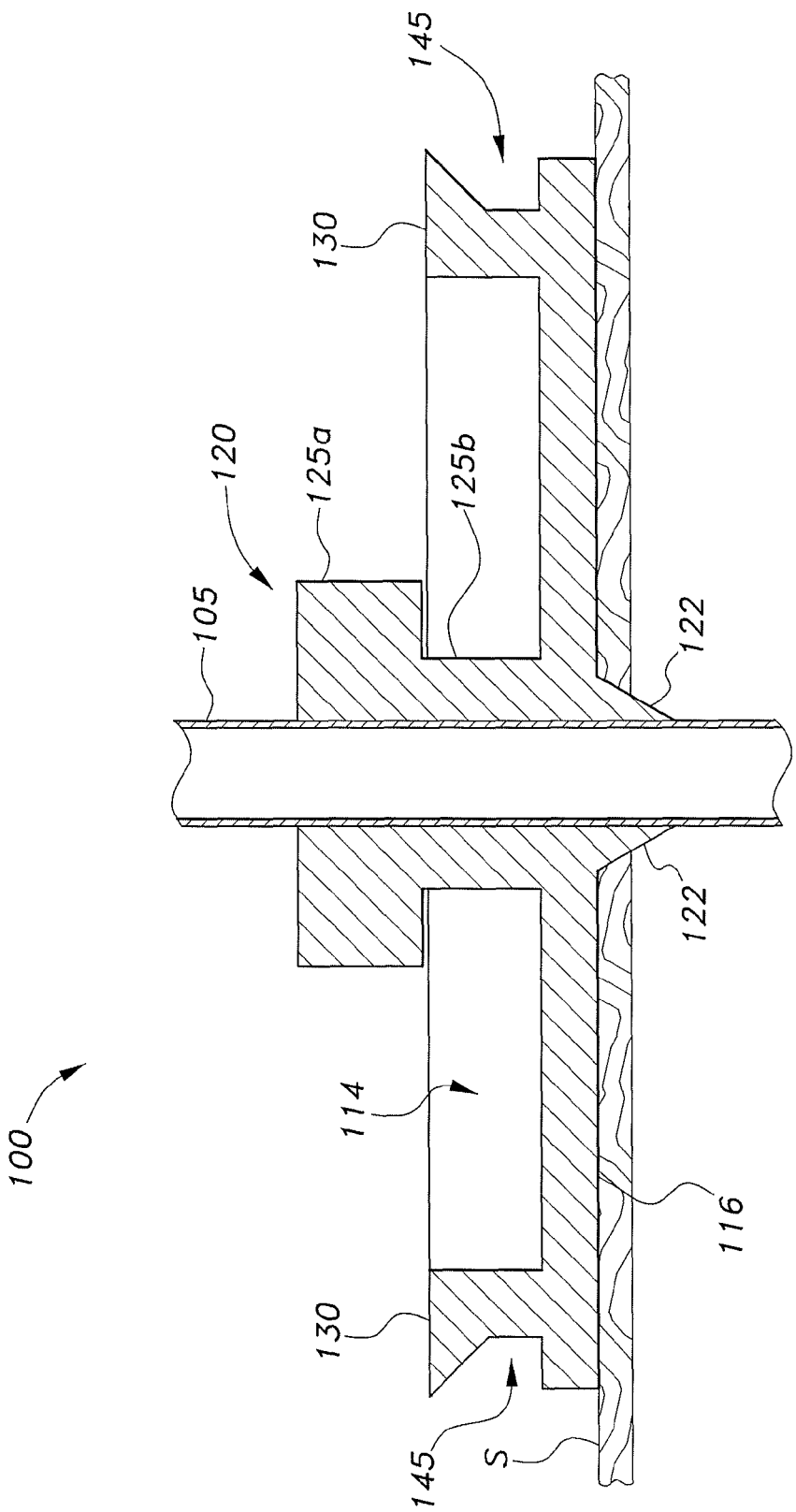
FIG. 5 is an environmental elevation view in section of the surgical drain anchoring device of FIG. 2, the tie securing the neck around the surgical drain tube being omitted.
Figure 6:
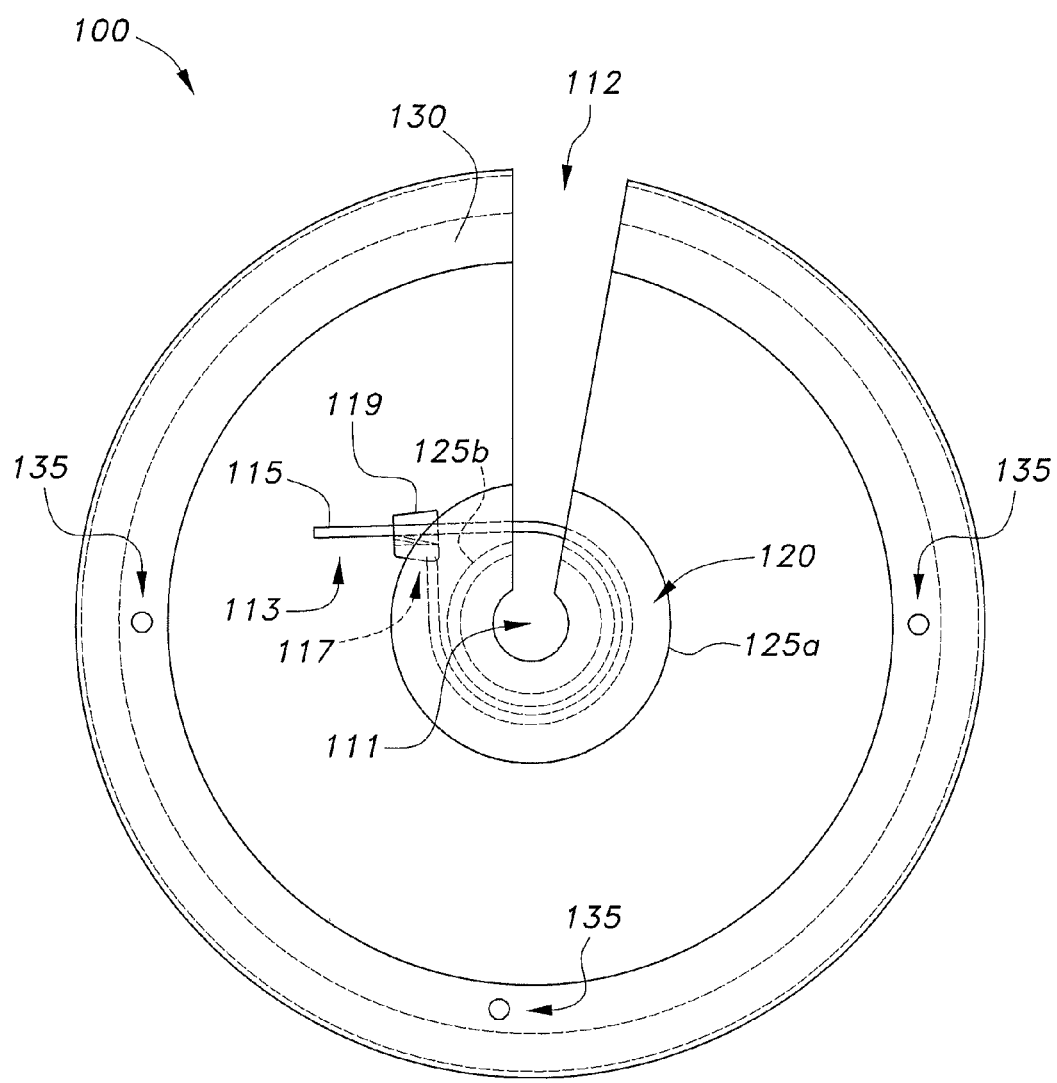
FIG. 6 is a top view of the surgical drain anchoring device of FIG. 2, shown before cinching the tie around the neck.

The device 100, including the pad, the neck 120, the annular tapered member 122, and the outer ridge 130 can be formed from any suitable, resilient, flexible, medical grade material, such as plastic, either as a monolithic body, or with the neck 120, tapered member 122, and outer ridge 130 permanently joined or fused to the pad. Further, the pad can have any suitable shape, such as a generally circular shape, and have any suitable dimensions. The lower surface 116 of the device 100 may include a layer of biocompatible adhesive so that the device 100 can be secured to the skin S of the patient P at the site where the surgical drain 105 exits the body. The tapered member 122 may extend through the skin S of the patient P to further secure the device 100 onto the patient P, as illustrated in FIGS. 4, 5, and 7B so that the device 100 can firmly anchor the surgical drain.

The neck member 120 positioned on the upper surface 114 of the device 100 has a substantially cylindrical body 125b and an annular flange above the body 125b defining a recess that is annular when the slit 112 is closed and configured for receiving the tie 113. The tie 113 includes a first end 115 having serrated teeth 118 and an opposing second end 117, the opposing second end 117 having a head 119 including a pawl so that as the teeth 118 ratchet through the pawl, the tie 113 is progressively cinched closed and the free first end 115 cannot reverse through the head 119, which might inadvertently open the neck 120, leaving the surgical drain tube insecure. The tie 113 can be formed from any suitable type of flexible medical grade material, such as nylon. The head 119 of the tie 113 may include a tab configured for loosening the tie 113 so that the device 100 can be removed after the drainage of the fluids is complete.

Figure 1:
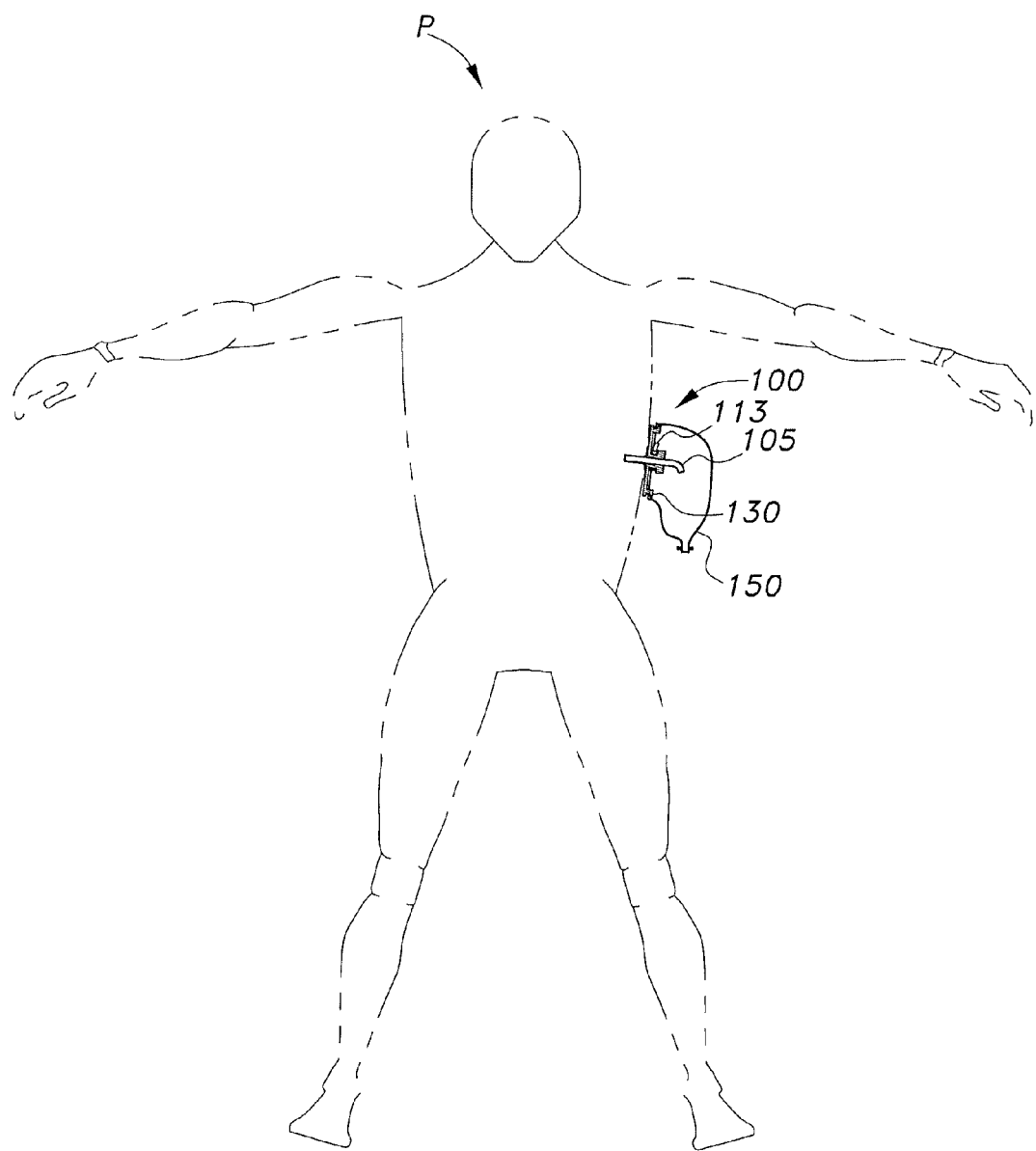
FIG. 1 is an environmental front view of a surgical drain anchoring device according to the present invention.
Figure 2:
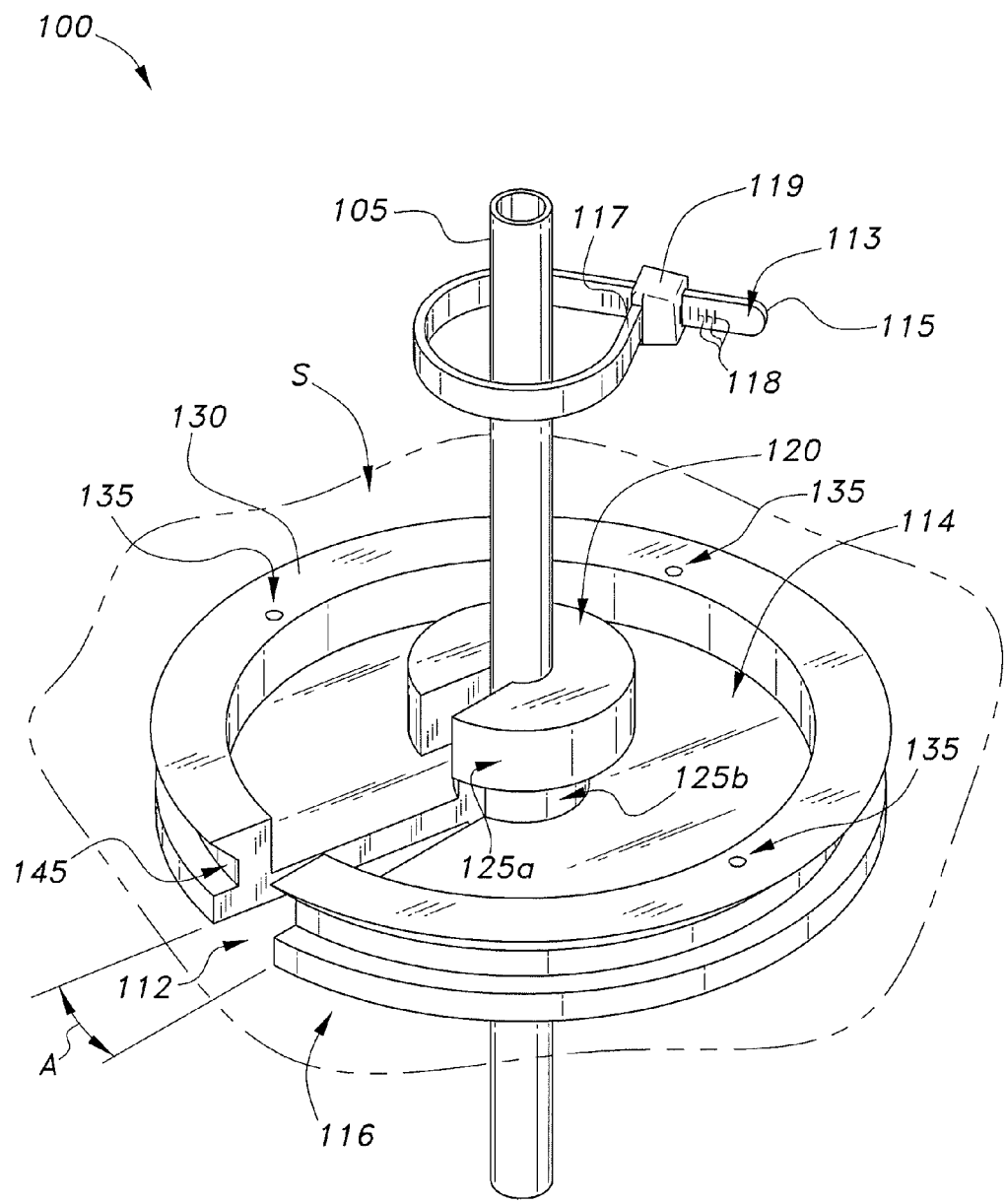
FIG. 2 is an environmental perspective view of a surgical drain anchoring device according to the present invention, shown with a drain tube extending through the device before cinching the tie around the neck of the device.
Figure 3:
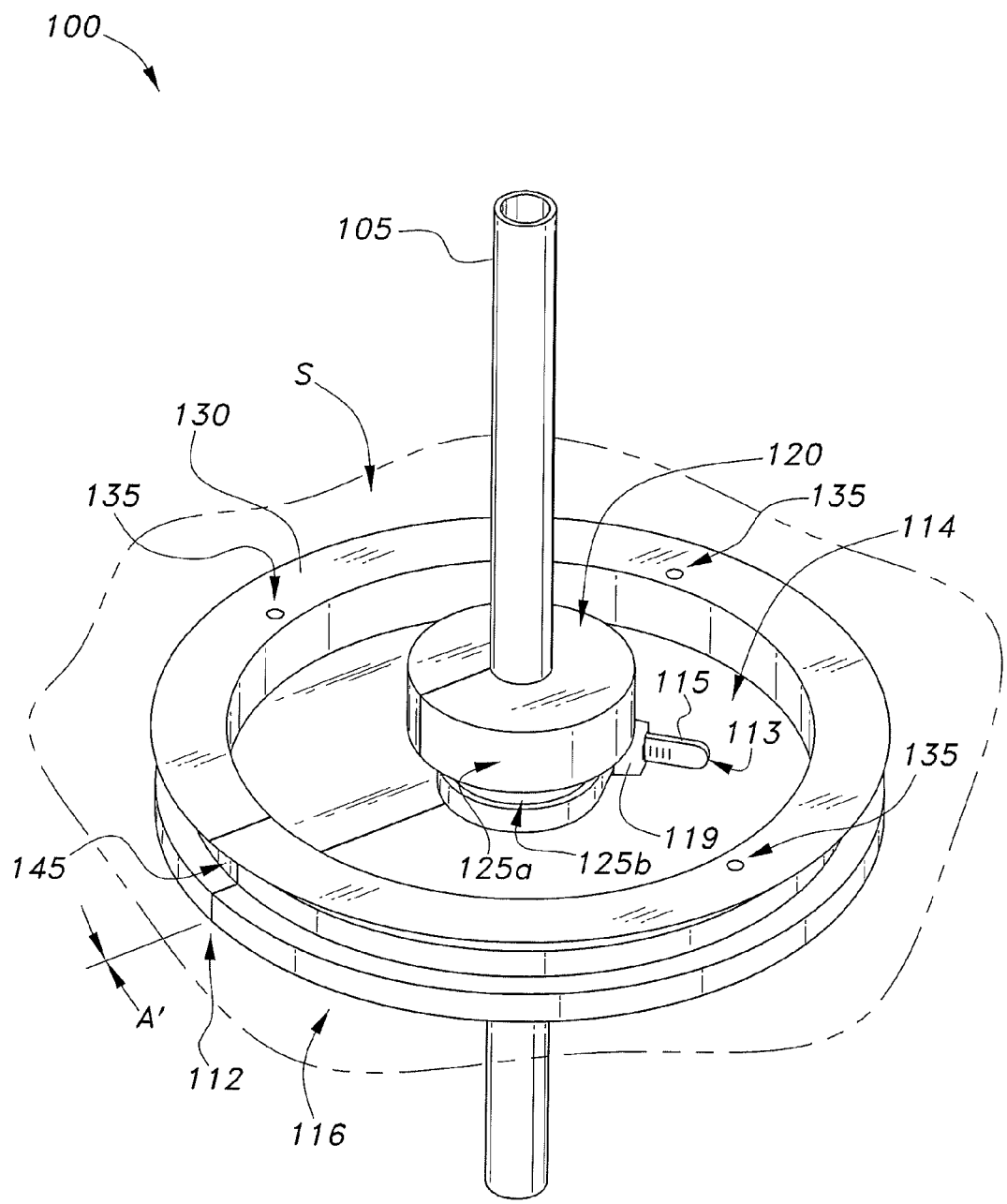
FIG. 3 is an environmental perspective view of the surgical drain anchoring device of FIG. 2, shown after cinching the tie around the neck to secure the anchoring device around the surgical drain tube.
Figure 7A:
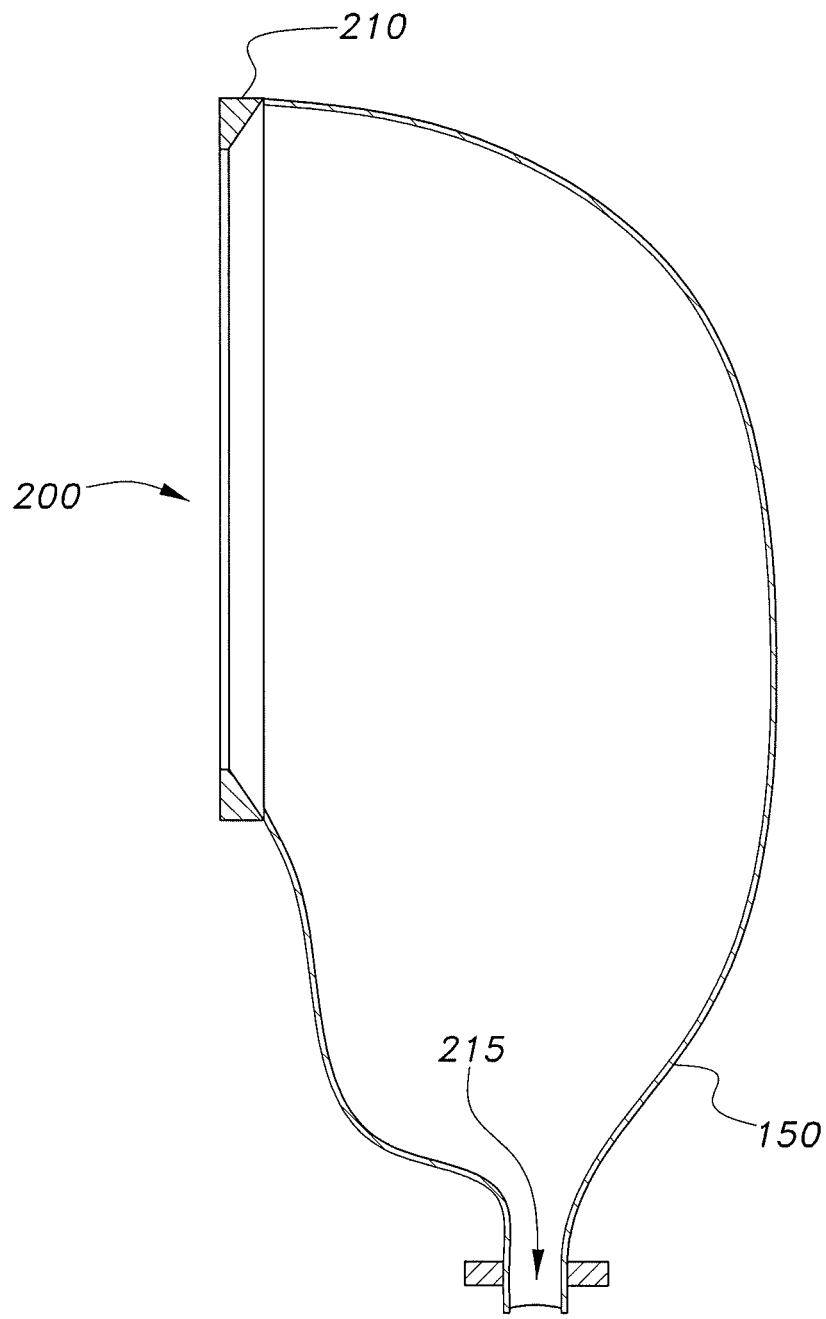
FIG. 7A is a side view in section of an external drainage bag for use with a surgical drain anchoring device according to the present invention.
Figure 7B:
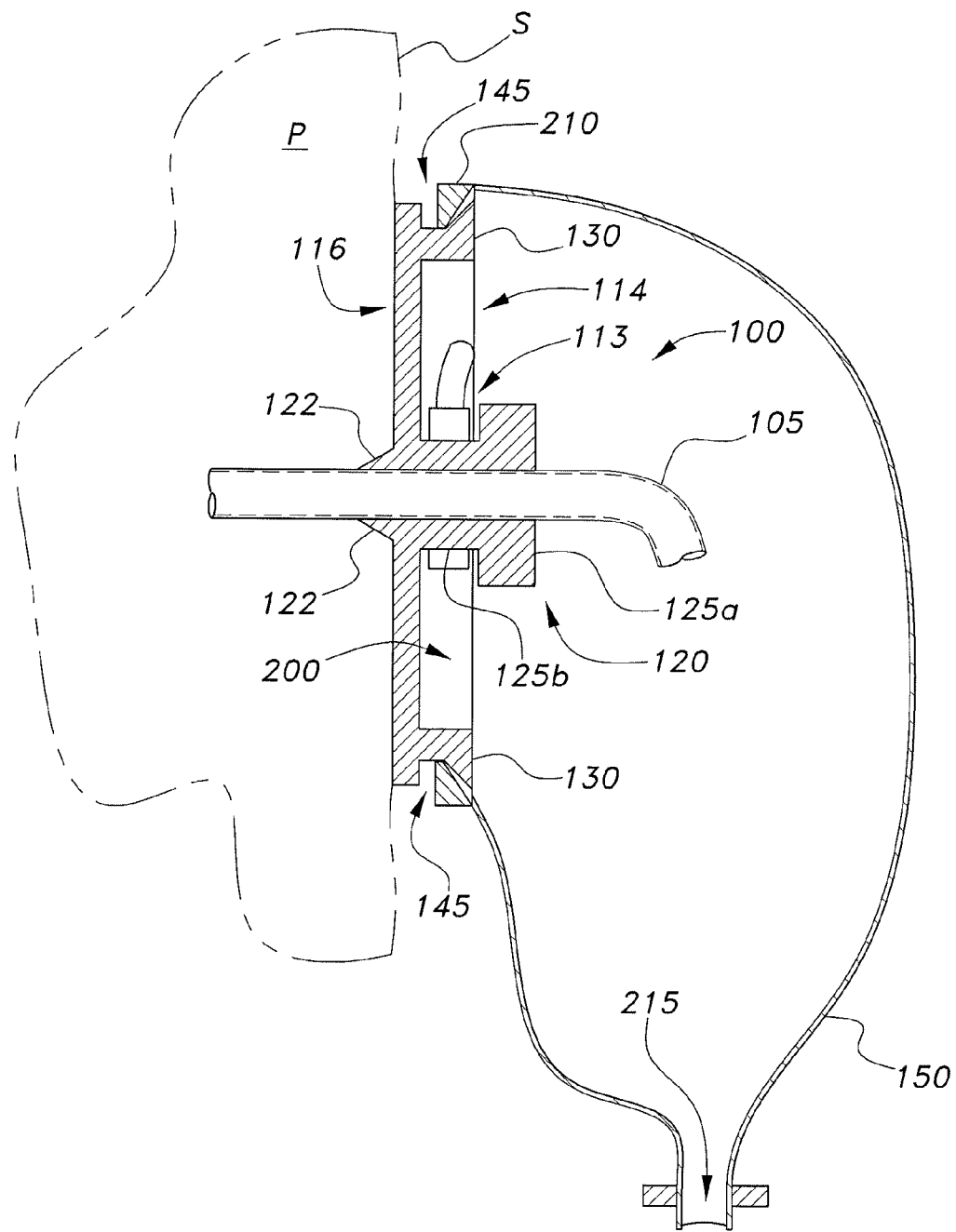
FIG. 7B is a diagrammatic environmental elevation view in section of the surgical drain anchoring device of FIG. 2, shown with a drainage bag attached to the device.

The outer ridge member 130 surrounding the neck member 120 of the device 100 can include an track 145 positioned along the exterior side of the outer ridge member 130, the track 145 being configured for receiving the drainage bag 150, as illustrated in FIGS. 1 and 7B. The outer ridge member 130 also includes a plurality of apertures 135 through which stiches (not shown) or staples (not shown) that can be inserted, if needed, to further secure the device 100 onto the skin S of the patient P.

By way of operation, once the surgical procedure has been completed and the surgical drain 105 has been inserted into the patient P to allow any gas or liquids to exit the body cavity of the patient P and drain freely from the body, the slit 112 of the device 100 of the device 110 is opened, as illustrated by arrow A, to attach the device 100 onto the surgical drain 105. After the device 100 is fitted onto the surgical drain 105, the device 100 is closed, as illustrated by arrow A', so that the aperture 111, as well as the central channel 140 of the neck member 120 of the device 100, completely surrounds the surgical drain 105. After the device 100 is closed around the surgical drain 105, the tie 113 secures the closure of the device 100 on the surgical drain 105. For example, a caregiver, such as nurse, can loop the first end 115 of the tie 113 around the body 125b of the neck member 120 to form a loop around the body 125b of the neck member 120 and then thread the first end 115 of the strap 113 through the head 119 at the opposing second end 117 of the strap 113 until the loop has tightened.

Once the device 100 is closed and secured onto the surgical drain 105, the device 100 is then secured onto the patient's P skin S surrounding the incision in which the surgical drain 105 was inserted. For example, the device 100 can be pressed against the skin so that adhesive on the lower surface 116 of the device 100 makes contact with the skin S and the tapered ends 122 on the lower surface 116 of the device 100 are inserted through the skin S of the patient to further secure the device 100 to the body of the patient P. It must be noted, if the adhesive and the tapered ends 122 on the lower surface 116 of the device 100 are unable to securely attach the device 100 onto the patient's P skin S, sutures (not shown) or staples (not shown) can be inserted through each aperture 135 of the outer ridge member 130 to further secure the device 100 onto the patient's P skin S.

The drainage bag 150 can then be attached to the outer ridge member 130 of the device 100 by any suitable means. For example, as illustrated in FIGS. 7A and 7B, the primary opening 200 of the drainage bag 150 can include an attachment member 210, such as a split ring, that can be securely positioned within the track 145 of the outer ridge member 130 of the device 100 to securely attach the drainage bag 150 to the device 100.

It is to be understood that the present invention is not limited to the embodiments described above, but encompasses any and all embodiments within the scope of the following claims.

I claim:
1. A surgical drain anchoring device, comprising:
a pad having a periphery, an upper surface and an opposing lower surface, the pad having a central aperture defined therein, the aperture being dimensioned and configured for extending a surgical drain tube therethrough;
a neck member extending from the upper surface of the pad, the neck member defining a central channel aligned with the aperture in the pad;
an annular tapered member extending from the lower surface of the pad, the annular tapered member being aligned with the aperture in the pad and the central channel defined in the neck member;
an outer annular ridge member extending from the upper surface of the pad, the outer ridge member being spaced apart from the neck member and having a track positioned outside the outer ridge member, the track being configured for receiving a drainage bag;
a slit extending radially through the neck member, the annular tapered member, the outer annular ridge member, and the pad from the aperture to the periphery of the pad, defining opposing sides of the slit, the opposing sides being capable of approximation to close the slit around the surgical drain tube so that the surgical drain tube extends through the pad, the neck member, and the annular tapered member; and a tie cinchable around the neck member to maintain the opposing sides of the slit approximated to secure the device around the surgical drain tube with the lower surface of the pad bearing against a patient's skin.

2. The surgical drain anchoring device according to claim 1, further comprising a drainage bag detachably connected to the track.

3. The surgical drain anchoring device according to claim 2, wherein the drainage bag includes a primary opening at a first end and a valve at an opposing second end.

4. The surgical drain anchoring device according to claim 1, wherein the tie comprises a first end having serrated teeth and an opposing second end having a pawl for engaging the teeth at the first end.

5. The surgical drain anchoring device according to claim 1, further comprising an adhesive on the lower surface of the pad.

6. A method of relieving gas or fluid accumulated in a body cavity of a patient, comprising:
   inserting a surgical drain into a patient; and
   securing the surgical drain anchoring device according to claim 1 to the surgical drain.

7. A surgical drain anchoring device, comprising:
   a pad having a periphery, an upper surface and an opposing lower surface, the pad having a central aperture defined therein, the aperture being dimensioned and configured for extending a surgical drain tube therethrough, the opposing lower surface including an adhesive;
   a neck member extending from the upper surface of the pad, the neck member defining a central channel aligned with the aperture in the pad;
   an annular tapered member extending from the lower surface of the pad, the annular tapered member being aligned with the aperture in the pad and the central channel defined in the neck member;
   an outer annular ridge member extending from the upper surface of the pad, the outer ridge member being spaced apart from the neck member and having a track positioned outside the outer ridge member;
   a drainage bag detachably secured to the track; and
   a slit extending radially through the neck member, the annular tapered member, the outer annular ridge member, and the pad from the aperture to the periphery of the pad, defining opposing sides of the slit, the opposing sides being capable of approximation to close the slit around the surgical drain tube so that the surgical drain tube extends through the pad, the neck member, and the annular tapered member.

8. The surgical drain anchoring device according to claim 7, further comprising
a tie cinchable around the neck member to maintain the opposing sides of the slit approximated to secure the device around the surgical drain tube with the lower surface of the pad bearing against a patient's skin.

9. The surgical drain anchoring device according to claim 8, wherein the tie comprises a first end having serrated teeth and an opposing second end having a pawl for engaging the teeth at the first end.

10. A method of relieving gas or fluid accumulated in a body cavity of a patient, comprising:
    inserting a surgical drain into a patient; and
    securing the surgical drain anchoring device according to claim 7 to the surgical drain.

11. A surgical drain anchoring device, comprising:
    a pad having a periphery, an upper surface and an opposing lower surface, the pad having a central aperture defined therein, the aperture being dimensioned and configured for extending a surgical drain tube therethrough, the opposing lower surface including an adhesive;
    a neck member extending from the upper surface of the pad, the neck member defining a central channel aligned with the aperture in the pad;
    an annular tapered member extending from the lower surface of the pad, the annular tapered member being aligned with the aperture in the pad and the central channel defined in the neck member;
    an outer annular ridge member extending from the upper surface of the pad, the outer ridge member being spaced apart from the neck member and having a track positioned outside the outer ridge member;
    a drainage bag detachably secured to the track;
    a slit extending radially through the neck member, the annular tapered member, the outer annular ridge member, and the pad from the aperture to the periphery of the pad, defining opposing sides of the slit, the opposing sides being capable of approximation to close the slit around the surgical drain tube so that the surgical drain tube extends through the pad, the neck member, and the annular tapered member; and
    a tie cinchable around the neck member to maintain the opposing sides of the slit approximated to secure the device around the surgical drain tube with the lower surface of the pad bearing against a patient's skin.

12. A method of relieving gas or fluid accumulated in a body cavity of a patient, comprising:
    inserting a surgical drain into a patient; and
    securing the surgical drain anchoring device according to claim 11 to the surgical drain.

* * * * *